US012582598B2

(12) United States Patent
Nam et al.

(10) Patent No.: US 12,582,598 B2
(45) Date of Patent: Mar. 24, 2026

(54) TOPICAL ANTI-INFLAMMATORY PHARMACEUTICAL COMPOSITION COMPRISING ZILEUTON

(71) Applicant: QURIENT CO., LTD., Gyeonggi-do (KR)

(72) Inventors: Kiyean Nam, Gyeonggi-do (KR); Jaeseung Kim, Seoul (KR); Chunwon Jung, Gyeonggi-do (KR); Jiyoong Chun, Gyeonggi-do (KR); Borami Jeon, Gyeonggi-do (KR)

(73) Assignee: QURIENT CO., LTD., Gyeonggi-Do (KR)

( * ) Notice: Subject to any disclaimer, the term of this patent is extended or adjusted under 35 U.S.C. 154(b) by 901 days.

(21) Appl. No.: 17/787,519

(22) PCT Filed: Dec. 30, 2019

(86) PCT No.: PCT/EP2019/087167
§ 371 (c)(1),
(2) Date: Jun. 20, 2022

(87) PCT Pub. No.: WO2021/121645
PCT Pub. Date: Jun. 24, 2021

(65) Prior Publication Data
US 2022/0387300 A1 Dec. 8, 2022

Related U.S. Application Data

(60) Provisional application No. 62/951,526, filed on Dec. 20, 2019.

(51) Int. Cl.
*A61K 9/00* (2006.01)
*A61K 9/06* (2006.01)
(Continued)

(52) U.S. Cl.
CPC .............. *A61K 9/0014* (2013.01); *A61K 9/06* (2013.01); *A61K 31/381* (2013.01); *A61K 47/14* (2013.01); *A61K 47/34* (2013.01); *A61P 17/00* (2018.01)

(58) Field of Classification Search
CPC ...... A61K 9/0014; A61K 9/06; A61K 31/381; A61K 47/14; A61K 47/34; A61P 17/00; A61P 17/06
See application file for complete search history.

(56) References Cited

U.S. PATENT DOCUMENTS

2007/0134341 A1 6/2007 Kipp et al.
2016/0324827 A1 11/2016 Nam et al.

FOREIGN PATENT DOCUMENTS

WO WO-2013056994 A1 * 4/2013 ............. A61K 47/14

OTHER PUBLICATIONS

Fleischer, A., et al. "Q301 (Zileuton) cream demonstrates superiority to vehicle in improving atopic dermatitis: Results from a phase 2A trial." Journal of the American Academy of Dermatology. vol. 81. No. 4. 360 Park Avenue South, New York, NY 10010-1710 USA: Mosby-Elsevier, 2019.
(Continued)

*Primary Examiner* — Deborah D Carr
(74) *Attorney, Agent, or Firm* — SALIWANCHIK, LLOYD & EISENSCHENK

(57) ABSTRACT

The present invention relates to a topical anti-inflammatory pharmaceutical composition comprising Zileuton. Furthermore, the present invention relates to uses of such composition. Moreover, the present invention relates to methods of preparing a topical anti-inflammatory pharmaceutical composition comprising Zileuton.

18 Claims, 1 Drawing Sheet

***P<0.001, Dexamethasone to Zileuton 1.0% cream Vs Acetone:
$P<0.05, $$$P<0.001, Acetone to Test article 8 SPC19 Vs Zileuton 1.0% cream
(compared using One-way ANOVA/Bonferronl's)

(51) Int. Cl.

| | |
|---|---|
| *A61K 31/381* | (2006.01) |
| *A61K 47/14* | (2017.01) |
| *A61K 47/34* | (2017.01) |
| *A61P 17/00* | (2006.01) |

(56) References Cited

OTHER PUBLICATIONS

Woodmansee, D. P., et al. "A pilot study examining the role of zileuton in atopic dermatitis." Annals of Allergy, Asthma & Immunology 83.6 (1999): pp. 548-552.

* cited by examiner

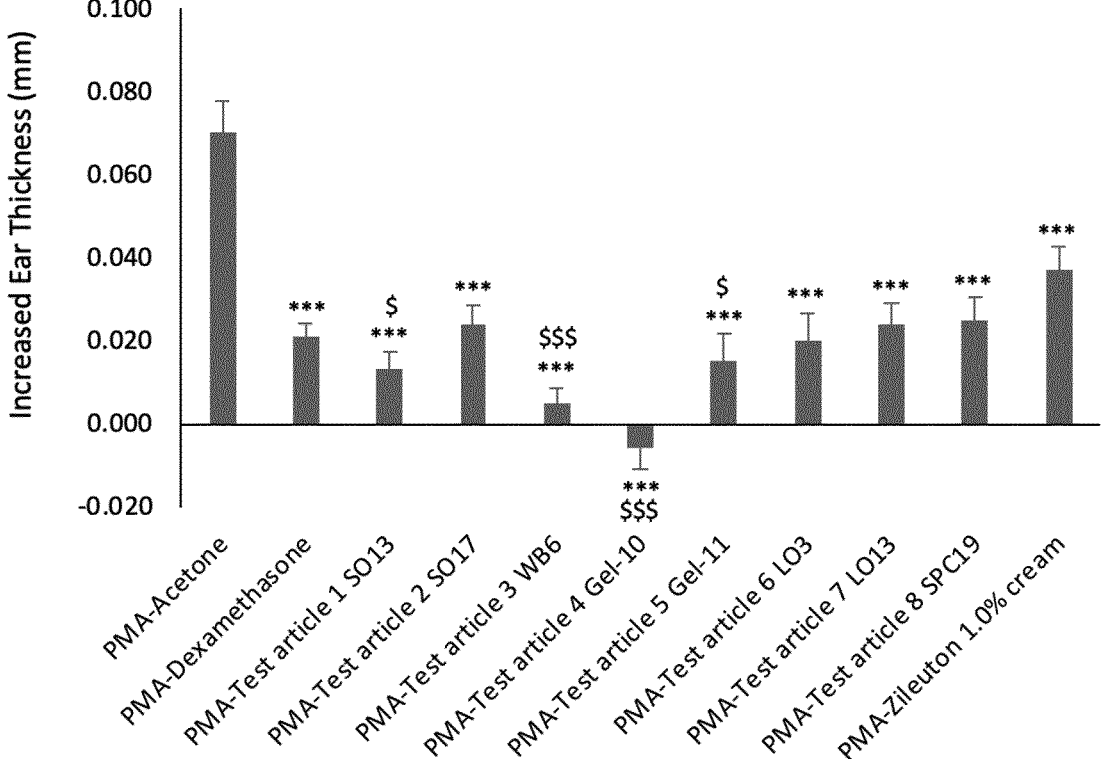
\*\*\*P<0.001, Dexamethasone to Zileuton 1.0% cream Vs Acetone:
$P<0.05, $$$P<0.001, Acetone to Test article 8 SPC19 Vs Zileuton 1.0% cream
(compared using One-way ANOVA/Bonferronl's)

TOPICAL ANTI-INFLAMMATORY PHARMACEUTICAL COMPOSITION COMPRISING ZILEUTON

CROSS REFERENCE TO RELATED APPLICATIONS

This application is a National Stage Application of International Application Number PCT/EP2019/087167, filed Dec. 30, 2019; which claims priority to U.S. Provisional Patent Application No. 62/951,526, filed Dec. 20, 2019.

The present invention relates to a topical anti-inflammatory pharmaceutical composition comprising Zileuton. Furthermore, the present invention relates to uses of such composition. Moreover, the present invention relates to methods of preparing a topical anti-inflammatory pharmaceutical composition comprising Zileuton.

Zileuton, also known as (±)-1-(1-(benzo[b]thiophen-2-yl) ethyl)-1-hydroxyurea, is an inhibitor of the enzyme 5-lipoxygenase which forms, inter alia, leukotrienes from arachidonic acid. Zileuton typically is a mixture of its (R)- and (S)-stereoisomer. Zileuton has been approved as an oral drug for the treatment of asthma and is known to improve pulmonary functions and symptoms in patients with mild to moderate asthma. Moreover, it has also been reported from clinical studies that patients having atopic dermatitis and being orally provided Zileuton, show an improvement of their atopic dermatitis symptoms. WO 2015/064898 describes Zileuton-containing compositions for topical administration. Numerous oral systemic administration forms have been developed, including also sustained release formulations (Qiu et al. 1997, Pharmaceutical Development and Technology, Vol. 2, pp. 197-204). However, Zileuton has significant hepatotoxicity, and thus requires a constant monitoring of liver functions, if the drug is administered as an oral administration form. Therefore, there continues to be a need in the art for alternative and improved formulations of Zileuton by which hepatotoxicity may be circumvented. In particular, there continuous to be a need in the art for topical administration forms Zileuton can be applied locally at efficiently high concentrations.

In a first aspect, the present invention relates to a topical anti-inflammatory pharmaceutical composition, comprising Zileuton at a concentration of >2% (w/w).

In one embodiment, Zileuton is present at a concentration in the range of from 2.1% (w/w) to 8% (w/w).

In one embodiment, Zileuton is present at a concentration in the range of from 2.5% (w/w) to 7.5% (w/w), preferably 3.0% (w/w) to 6.0% (w/w), more preferably 4.5% (w/w) to 5.5% (w/w).

In one embodiment, the pharmaceutical composition is formulated as a topical formulation selected from solution ointment, suspension ointment, solution cream, suspension cream, water/buffer solution cream, gel and lotion.

In one embodiment, the pharmaceutical composition is formulated as a solution ointment and comprises an organic solvent, a thickening agent and a solubilizer.

The composition according to claim 5, which further comprises at least one of an emulsifier and an oil.

In one embodiment of the solution ointment, the organic solvent is present in said composition in a range of from 2% (w/w) to 70% (w/w), the thickening agent is present in said composition in a range of from 10% (w/w) to 70% (w/w) and the solubilizer is present in said composition in a range of from 0.1% (w/w) to 2% (w/w).

In one embodiment of the solution ointment, the organic solvent is present in said composition in a range of from 40% (w/w) to 60% (w/w), the thickening agent is present in said composition in a range of from 35% (w/w) to 55% (w/w) and the solubilizer is present in said composition in a range of from 0.5% (w/w) to 1.5% (w/w).

In one embodiment of the solution ointment, the organic solvent is selected from diethylene glycol mono ethyl ether, polyethylene glycol 200, polyethylene glycol 300, polyethylene glycol 400, propylene glycol, hexylene glycol, dimethyl sulfoxide, N-methyl-2-pyrrolidone, dimethyl formamide, dimethyl acetamide, and mixtures of any of the foregoing.

In one embodiment of the solution ointment, the thickening agent is selected from stearyl alcohol, beeswax polyethylene glycol-8, polyethylene glycol 1500, polyethylene glycol 3350, polyethylene glycol 6000, polyethylene glycol 8000, polyacrylic acid, glyceryl mono and di stearate, stearic acid, cetyl alcohol, mono and diglycerides, lanolin, white vaseline, paraffin, and mixtures of any of the foregoing.

In one embodiment of the solution ointment, the solubilizer is polyvinyl caprolactam-polyvinyl acetate-polyethylene glycol graft copolymer.

In one embodiment, the emulsifier is selected from ethylene glycol palmitostearate, propylene glycol monolaurate, sorbitan monolaurate, sorbitane monooleate, and mixtures of any of the foregoing.

In one embodiment of the solution ointment, the oil is selected from corn oil, castor oil, linoleoyl polyoxyl-6 glycerides, medium chain triglycerides, propylene glycol dicaprylate, glyceryl monocaprate type I, propylene glycol monocaprylate type II, caprylocaproyl polyoxyl glycerides, caprylic glycerides, oleic acid, ethyl oleate, liquid paraffin, isopropyl myristate, and mixtures of any of the foregoing.

In another embodiment, the pharmaceutical composition is formulated as a suspension ointment and comprises a thickening agent and an oil.

In one embodiment of the suspension ointment, the composition further comprises an emulsifier.

In one embodiment of the suspension ointment, the thickening agent is present in said composition in a range of from 5% (w/w) to 60% (w/w).

In one embodiment of the suspension ointment, the thickening agent is present in said composition in a range of from 8% (w/w) to 47% (w/w).

In one embodiment of the suspension ointment, the oil is present in said composition in a range of from 30% (w/w) to 50% (w/w), preferably from 35% (w/w) to 45% (w/w).

In one embodiment of the suspension ointment, the thickening agent is selected from polyacrylic acid, cetyl alcohol, stearyl alcohol, paraffin, beeswax polyethylene glycol-8, white wax, mono and diglycerides, stearic acid, glyceryl mono and di stearate, lanolin, white vaseline, and mixtures of any of the foregoing.

In one embodiment of the suspension ointment, the oil is selected from castor oil, oleic acid, linoleoyl polyoxyl-6 glycerides, medium chain triglycerides, ethyl oleate, propylene glycol dicaprylate, glyceryl monolinoleate, liquid paraffin, olive oil, oleoyl polyoxyl-6 glycerides, lauroyl polyoxyl-6 glycerides, peceol, glyceryl monocaprate type I, Isopropyl myristate, and mixtures of any of the foregoing.

In one embodiment of the suspension ointment, the emulsifier is selected from ethylene glycol palmitostearate, propylene glycol monolaurate, sorbitan monolaurate, sorbitane monooleate, and mixtures of any of the foregoing.

In yet another embodiment, the pharmaceutical composition is formulated as a solution cream and comprises an organic solvent, a thickening agent, an emulsifier and a solubilizer.

In one embodiment of the solution cream, the composition further comprises an oil.

In one embodiment of the solution cream, the organic solvent is present in said composition in a range of from 7% (w/w) to 40% (w/w), the thickening agent is present in said composition in a range of from 4% (w/w) to 52% (w/w), the emulsifier is present in said composition in a range of from 5% (w/w) to 40% (w/w) and the solubilizer is present in said composition in a range of from 0.1% (w/w) to 2% (w/w).

In one embodiment of the solution cream, the organic solvent is present in said composition in a range of from 7% (w/w) to 32% (w/w), the thickening agent is present in said composition in a range of from 8% (w/w) to 47% (w/w), the emulsifier is present in said composition in a range of from 7% (w/w) to 36% (w/w) and the solubilizer is present in said composition in a range of from 0.5% (w/w) to 1.5% (w/w).

In one embodiment of the solution cream, the organic solvent is selected from ethanol, diethylene glycol monoethyl ether, propylene glycol, hexylene glycol, polyethylene glycol 200, polyethylene glycol 300, polyethylene glycol 400, N-methyl-2-pyrrolidone, dimethyl formamide, dimethyl acetamide, and mixtures of any of the foregoing.

In one embodiment of the solution cream, the thickening agent is selected from cetyl alcohol, stearyl alcohol, paraffin, beeswax polyethylene glycol-8, mono and diglycerides, white wax, stearic acid, glyceryl mono and di stearate, polyethylene glycol 1500, polyethylene glycol 3350, polyethylene glycol 6000, lanolin, white vaseline, and mixtures of any of the foregoing.

In one embodiment of the solution cream, the emulsifier is selected from ethylene glycol palmitostearate, sorbitan monolaurate, sorbitane monooleate, polyethylene glycol octadecyl ether, caprylocaproyl polyoxyl glycerides, polyoxyl 35 hydrogenated castor oil, polyethylene glycol-40 hydrogenated castor oil, sodium lauryl sulfate, polyethylene glycol sorbitan monolaurate, polyoxy ethylene sorbitan monooleate, d-a-tocopheryl polyethylene glycol 1000 succinate, triethanolamine, lecithin from egg, lecithin from soybean, poly-oxyethylene esters of 12-hydroxystearic acid, poloxamer 407, poloxamer 188, propylene glycol monolaurate, and mixtures of any of the foregoing.

In one embodiment of the solution cream, the solubilizer is polyvinyl caprolactam-polyvinyl acetate-polyethylene glycol graft copolymer.

In one embodiment of the solution cream, the oil is selected from corn oil, linoleoyl polyoxyl-6 glycerides, medium chain triglycerides, ethyl oleate, propylene glycol dicaprylate, glyceryl monocaprate type I, propylene glycol monocaprylate type II, caprylocaproyl polyoxyl glycerides, caprylic glyceride, glyceryl monolinoleate, peceol, isopropyl myristate, and mixtures of any of the foregoing.

In yet another embodiment, the pharmaceutical composition is formulated as a suspension cream and comprises an organic solvent, a thickening agent and an emulsifier.

In one embodiment of the suspension cream, the composition further comprises an oil.

In one embodiment of the suspension cream, the organic solvent is present in said composition in a range of from 15% (w/w) to 30% (w/w), the thickening agent is present in said composition in a range of from 25% (w/w) to 45% (w/w) and the emulsifier is present in said composition in a range of from 5% (w/w) to 40% (w/w).

In one embodiment of the suspension cream, the organic solvent is present in said composition in a range of from 18% (w/w) to 27% (w/w), the thickening agent is present in said composition in a range of from 28% (w/w) to 42%

(w/w) and the emulsifier is present in said composition in a range of from 8% (w/w) to 32% (w/w).

In one embodiment of the suspension cream, the organic solvent is selected from ethanol, glycerin, diethylene glycol monoethyl ether, propylene glycol, hexylene glycol, polyethylene glycol 200, polyethylene glycol 300, polyethylene glycol 400, and mixtures of any of the foregoing.

In one embodiment of the suspension cream, the thickening agent is selected from cetyl alcohol, stearyl alcohol, paraffin, beeswax polyethylene glycol-8, white wax, mono and diglycerides, stearic acid, glyceryl mono and di stearate, lanolin, white vaseline, and mixtures of any of the foregoing.

In one embodiment of the suspension cream, the emulsifier is selected from sorbitan monolaurate, sorbitane monooleate, polyoxyl 35 hydrogenated castor oil, polyethylene glycol-40 hydrogenated castor oil, sodium lauryl sulfate, polyethylene glycol octadecyl ether, lauroyl polyoxyl-32 glycerides, lecithin from egg, lecithin from soybean, polyethylene glycol sorbitan monolaurate, polyoxy ethylenesorbitan monostearate, polyoxyethylenesorbitan monooleate, d-a-tocopheryl polyethylene glycol 1000 succinate, 2-hydroxypropyl-β-cyclodextrin, sulfobutylether-β-cyclodextrin, poloxamer 407, poloxamer 188, poly-oxyethylene esters of 12-hydroxystearic acid, triethanolamine, propylene glycol monolaurate, and mixtures of any of the foregoing.

In one embodiment of the suspension cream, the oil is selected from medium chain triglycerides, glyceryl monolinoleate, liquid paraffin, peceol, caprylic glycerides, isopropyl myristate, castor oil, oleic acid, olive oil, linoleoyl polyoxyl-6 glycerides, oleoyl polyoxyl-6 glycerides, lauroyl polyoxyl-6 glycerides, ethyl oleate, propylene glycol dicaprylate, and mixtures of any of the foregoing.

In yet another embodiment, the pharmaceutical composition is formulated as a water/buffer solution cream formulation and comprises an aqueous solvent and an emulsifier.

In one embodiment of the water/buffer solution cream formulation, the composition further comprises at least one of an organic solvent, a thickening agent and an oil.

In one embodiment of the water/buffer solution cream formulation, said water/buffer solution cream formulation comprises an organic solvent, an aqueous solvent, a thickening agent and an emulsifier.

In one embodiment of the water/buffer solution cream formulation, the aqueous solvent is present in said composition in a range of from 2% (w/w) to 16% (w/w) and the emulsifier is present in said composition in a range of from 5% (w/w) to 70% (w/w).

In one embodiment of the water/buffer solution cream formulation, the aqueous solvent is present in said composition in a range of from 4% (w/w) to 13% (w/w) and the emulsifier is present in said composition in a range of from 7% (w/w) to 67% (w/w).

In one embodiment of the water/buffer solution cream formulation, the organic solvent is present in said composition in a range of from 18% (w/w) to 22% (w/w), the aqueous solvent is present in said composition in a range of from 5% (w/w) to 7% (w/w), the thickening agent is present in said composition in a range of from 12% (w/w) to 16% (w/w) and the emulsifier is present in said composition in a range of from 53% (w/w) to 60% (w/w).

In one embodiment of the water/buffer solution cream formulation, the aqueous solvent is water or a pH buffered solution in a range from pH 2.0 to 8.0.

In one embodiment of the water/buffer solution cream formulation, the pH buffered solution is acid phthalate buffer (pH4.0), acetate buffer (pH 4.1), citrate buffer (pH4.0), phosphate buffer (pH6.0), and Merck buffer (pH4.0).

In one embodiment of the water/buffer solution cream formulation, the emulsifier is selected from ethylene glycol palmitostearate, sorbitan monolaurate, sorbitane monooleate, caprylocaproyl polyoxyl glycerides, polyoxyl 35 hydrogenated castor oil, polyethylene glycol-40 hydrogenated castor oil, lecithin from egg, polyethylene glycol sorbitan monolaurate, polyoxy ethylene sorbitan monostearate, polyoxy ethylene sorbitan monooleate, d-a-tocopheryl polyethylene glycol 1000 succinate, poly-oxyethylene esters of 12-hydroxystearic acid, poloxamer 407, triethanolamine, sodium lauryl sulfate, lauroyl polyoxyl-32 glycerides, and mixtures of any of the foregoing.

In one embodiment of the water/buffer solution cream formulation, the organic solvent is selected from ethanol, diethylene glycol monoethyl ether, propylene glycol, polyethylene glycol 200, polyethylene glycol 300, polyethylene glycol 400, N-methyl-2-pyrrolidone, dimethyl acetamide, dimethyl formamide, hexylene glycol, and mixtures of any of the foregoing.

In one embodiment of the water/buffer solution cream formulation, the thickening agent is selected from white wax, beeswax polyethylene glycol-8, cetyl alcohol, stearyl alcohol, glyceryl mono and di stearate, polyethylene glycol 1500, polyethylene glycol 3350, polyethylene glycol 6000, lanolin, white vaseline, and mixtures of any of the foregoing.

In one embodiment of the water/buffer solution cream formulation, the oil is selected from medium chain triglycerides, ethyl oleate, propylene glycol dicaprylate, glyceryl monocaprate type I, propylene glycol monocaprylate type II, caprylocaproyl polyoxylglycerides, caprylic glycerides, isopropyl myristate, corn oil, linoleoyl polyoxyl-6 glycerides, glyceryl monolinoleate, and mixtures of any of the foregoing.

In yet a further embodiment, the pharmaceutical composition is formulated as a gel formulation and comprises an aqueous solvent and a viscosity controlling agent.

In one embodiment of the gel formulation, the composition further comprises an organic solvent and an emulsifier.

In one embodiment of the gel formulation, said gel formulation comprises an organic solvent, an aqueous solvent, a viscosity controlling agent and an emulsifier.

In one embodiment of the gel formulation, the aqueous solvent is present in said composition in a range of from 5% (w/w) to 70% (w/w) and the viscosity controlling agent is present in said composition in a range of from 2% (w/w) to 33% (w/w).

In one embodiment of the gel formulation, the aqueous solvent is present in said composition in a range of from 8% (w/w) to 62% (w/w) and the viscosity controlling agent is present in said composition in a range of from 4% (w/w) to 31% (w/w).

In one embodiment of the gel formulation, the organic solvent is present in said composition in a range of from 52% (w/w) to 57% (w/w), the aqueous solvent is present in said composition in a range of from 14% (w/w) to 19% (w/w), the viscosity controlling agent is present in said composition in a range of from 2% (w/w) to 6% (w/w) and the emulsifier is present in said composition in a range of from 18% (w/w) to 22% (w/w).

In one embodiment of the gel formulation, the aqueous solvent is water or a pH buffered solution in a range from pH 2.0 to 8.0.

In one embodiment of the gel formulation, the pH buffered solution is selected from 0.01N HCl (pH 2.0), sodium citrate buffer (pH 4.0), phosphate buffer (pH 6.0), and phosphate buffer (pH 7.5).

In one embodiment of the gel formulation, the viscosity controlling agent is selected from acrylic acid polymer, methylcellulose 400 cP, methylcellulose 4000 cP, hydroxypropyl methyl cellulose K4M, hydroxypropyl methyl cellulose K15M, sodium carboxymethyl cellulose, gum acacia, and mixtures of any of the foregoing.

In one embodiment of the gel formulation, the organic solvent is selected from ethanol, diethylene glycol monoethyl ether, propylene glycol, polyethylene glycol 200, polyethylene glycol 300, polyethylene glycol 400, N-methyl-2-pyrrolidone, dimethyl formamide, dimethyl acetamide, and mixtures of any of the foregoing.

In one embodiment of the gel formulation, the emulsifier is selected from poly-oxyethylene esters of 12-hydroxystearic acid, triethanolamine, caprylocaproyl polyoxyl glycerides, polyoxyl 35 hydrogenated castor oil, polyethylene glycol-40 hydrogenated castor oil, polyoxy ethylene sorbitan monooleate, d-a-tocopheryl polyethylene glycol 1000 succinate, and mixtures of any of the foregoing.

In yet another embodiment, the pharmaceutical composition is formulated as a lotion formulation and comprises an organic solvent.

In one embodiment of the lotion formulation, the composition further comprises at least one of an aqueous solvent, an emulsifier and an oil.

In one embodiment of the lotion formulation, said lotion formulation comprises an organic solvent, an aqueous solvent and an emulsifier.

In one embodiment of the lotion formulation, the organic solvent is present in said composition in a range of from 10% (w/w) to 80% (w/w).

In one embodiment of the lotion formulation, the organic solvent is present in said composition in a range of from 13% (w/w) to 77% (w/w).

In one embodiment of the lotion formulation, the organic solvent is present in said composition in a range of from 45% (w/w) to 55% (w/w), the aqueous solvent is present in said composition in a range of from 18% (w/w) to 22% (w/w) and the emulsifier is present in said composition in a range of from 23% (w/w) to 27% (w/w).

In one embodiment of the lotion formulation, the organic solvent is selected from ethanol, diethylene glycol monoethyl ether, propylene glycol, hexylene glycol, polyethylene glycol 200, polyethylene glycol 300, polyethylene glycol 400, polyethylene glycol 1500, polyethylene glycol 3350, N-methyl-2-pyrrolidone, dimethyl formamide, dimethyl acetamide, and mixtures of any of the foregoing.

In one embodiment of the lotion formulation, the aqueous solvent is water or a pH buffered solution in a range from pH 2.0 to 8.0.

In one embodiment of the lotion formulation, the pH buffered solution is selected from acid phthalate buffer (pH 4.0), acetate buffer (pH 4.1), citrate buffer (pH 4.0), phosphate buffer (pH 6.0) and merck buffer pH (4.0).

In one embodiment of the lotion formulation, the emulsifier is selected from sorbitan monolaurate, caprylocaproyl polyoxylglycerides, sodium lauryl sulfate, polyethylene glycol octadecyl ether, lecithin from soybean, polyoxyl 35 hydrogenated castor oil, polyethylene glycol-40 hydrogenated castor oil, polyoxyethylenesorbitan monostearate, poly-oxyethylene esters of 12-hydroxystearic acid, polyoxyethylenesorbitan monooleate, d-a-tocopheryl polyethylene glycol 1000 succinate, triethanolamine, propylene glycol monolaurate, and mixtures of any of the foregoing.

In one embodiment of the lotion formulation, the oil is selected from glyceryl monocaprate type I, propylene glycol monocaprylate type II, caprylocaproyl polyoxyl glycerides, and mixtures of any of the foregoing.

In one aspect according to the present invention, the composition is formulated for topical application to human skin.

In one embodiment, Zileuton is racemic Zileuton.

In a further aspect, the present invention also relates to the topical anti-inflammatory pharmaceutical composition according to any of the foregoing embodiments, for use in a method of treatment of a skin disease, wherein said method comprises comprises administering, to a subject in need of such treatment, a composition of any of the foregoing embodiments.

In one embodiment, said disease is selected from atopic dermatitis, acne, urticaria, psoriasis, eczema, a bullous skin disease, collagenoses, Sjogren-Larsson syndrome, or acne in skin lesions of mastocytosis, and said method preferably comprises administering, to a subject in need of such treatment, a composition of any of the foregoing embodiments.

In one embodiment, the composition is applied topically to human skin.

In a further aspect, the present invention also relates to a method of treatment of a skin disease, wherein said method comprises comprises administering, to a subject in need of such treatment, a composition of any of the foregoing embodiments.

In yet a further aspect, the present also relates to the use of a composition according to any of the foregoing embodiments for the manufacture of a medicament for the treatment of a skin disease, wherein such skin disease preferably is selected from atopic dermatitis, acne, urticaria, psoriasis, eczema, a bullous skin disease, collagenoses, Sjogren-Larsson syndrome, or acne in skin lesions of mastocytosis.

In yet a further aspect, the present invention relates to a method of preparing a topical anti-inflammatory pharmaceutical composition according to any of the foregoing embodiments, said method comprising the following steps: heating ingredients and solvents, mixing Zileuton and dissolved ingredients as well as cooling mixed Zileuton and ingredients.

In one embodiment, said method of preparing comprises the following steps: heating ingredients and solvents under heating condition of temperature of 25° C. to 100° C., mixing Zileuton and dissolved ingredients under mixing condition of temperature of 25° C. to 100° C. with 100 rpm to 5000 rpm of mixing speed as well as cooling mixed Zileuton and ingredients to 0° C. to 50° C.

In one embodiment, said method of preparing comprises the following steps: heating ingredients and solvents under heating condition of temperature of 40° C. to 80° C., mixing Zileuton and dissolved ingredients under mixing condition of temperature of 40° C. to 80° C. with 250 rpm to 2500 rpm of mixing speed as well as cooling mixed Zileuton and ingredients to 10° C. to 40° C.

In one embodiment, said method of preparing comprises comprising the following steps: heating ingredients and solvents under heating condition of temperature of 50° C. to 70° C. mixing Zileuton and dissolved ingredients under mixing condition of temperature of 50° C. to 70° C. with 1000 rpm to 1500 rpm of mixing speed as well as cooling mixed Zileuton and ingredients to 20° C. to 30° C.

The present inventors have managed to provide a number of topical compositions comprising Zileuton which show excellent anti-inflammatory properties when applied topically in an animal model. In particular, the compositions in accordance with the present invention were particularly suitable for treating inflammatory symptoms of the skin. The present inventors managed to provide various formulations that appear to be particularly suitable for topical administration to the skin.

As used herein, the term "ointment" refers to a topical composition that has little or no water solubility, as a result of which such composition has the capability of remaining on the skin, even when the skin is exposed to water. Ointments are particularly suitable where such water-resistance is desired.

The term "cream" refers to a topical formulation which, in comparison to an "ointment" has a higher water-solubility. In other words, such a "cream" can be more easily washed off having been applied to the skin.

A "gel", as used herein, is meant to refer to a dispersion comprising a solid and a liquid phase. More specifically, and in particular, "gels" according to embodiments of the present invention are "hydrogels", i. e. gels in which the solid phase is water or an aqueous solution. In another embodiment, "gels" in accordance with the present invention may also involve an oil part and may therefore be in some instances "oily gels" rather than "hydrogels".

The term "lotion" is a generally water-soluble composition that, in comparison to "creams" has a higher water-solubility.

The term "mixtures of . . . ", when used herein in the context of mixtures of components, such as solvents, emulsifiers etc. is meant to refer to mixtures that include at least two or more such components (e.g. solvents, emulsifiers etc.). For example, a mixture of solvents may mean that there are two or three or four or even more different solvents in such mixture.

Moreover, reference is made to the FIGURE which shows the effect of various Zileuton-containing formulations on phorbol ester induced ear edema in ICR mice. The abbreviations SO13, SO17, WB6, Gel-10, Gel-11, LO3, LO13 and SPC19 used in the FIGURE refer to the formulations: solution ointment 13, solution ointment 17, water-buffered solution cream 6, gel 10, gel 11, lotion 3, lotion 13 and suspension cream 19, respectively, described herein further. The formulations in accordance with embodiments of the present invention showed excellent results in terms of a reduction of the ear swelling response (caused by exposure to phorbol ester).

Moreover, reference is made to the examples which are meant to further illustrate, not to limit the present invention.

There follows a series of examples that serve to illustrate the invention.

EXAMPLE 1

Solubility of Zileuton in Various Solvents

Approximately solubility of the Zileuton was measured in different vehicles. Semi-soild and waxy solid excipients were melted and tested at 50° C. or 70° C.

| Vehicle | Temp. | HLB | Approximate Solubility (mg/mL) |
|---|---|---|---|
| Medium chain triglycerides | 25° C. | 1 | S < 5 |
| Linoleoyl polyoxyl-6 glycerides | 25° C. | 9 | S < 5 |
| Oleoyl polyoxyl-6 glycerides | 25° C. | 4 | S < 5 |

-continued

| Vehicle | Temp. | HLB | Approximate Solubility (mg/mL) |
|---|---|---|---|
| Corn oil | 25° C. | / | S < 5 |
| Castor oil | 25° C. | / | S < 5 |
| Oleic acid | 25° C. | / | S < 5 |
| Olive oil | 25° C. | / | S < 5 |
| Propylene glycol monolaurate | 25° C. | 3 | 8.3 < S < 12.5 |
| Peceol | 25° C. | 1 | S < 5 |
| Glyceryl monocaprate type I | 25° C. | / | 8.3 < S < 12.5 |
| Propylene glycol monocaprylate type II | 25° C. | / | 12.5 < S < 25 |
| Hexylene glycol | 25° C. | / | 25 < S < 50 |
| Isopropyl myristate | 25° C. | / | S < 5 |
| Sorbitan monolaurate | 25° C. | ~8 | S < 5 |
| Sorbitane monooleate | 25° C. | ~4 | S < 5 |
| Glyceryl monolinoleate | 25° C. | ~1 | S < 5 |
| Liquid paraffin | 25° C. | / | S < 5 |
| Ethyl oleate | 25° C. | / | S < 5 |
| Propylene glycol dicaprylate | 25° C. | 1 | S < 5 |
| Lauroyl polyoxyl-6 glycerides | 50° C. | 9 | S < 10 |
| Caprylic glycerides | 50° C. | / | 18.2 < S < 28.6 |
| Caprylocaproyl polyoxyl glycerides | 25° C. | ~14 | 40 < S < 66.7 |
| Polyoxyl 35 hydrogenated castor oil | 25° C. | ~14 | 12.5 < S < 14.3 |
| Polyethylene glycol octadecyl ether | 25° C. | ~15 | 10 < S < 11.1 |
| Polyethylene glycol sorbitan monolaurate | 25° C. | ~16 | 12.5 < S < 14.3 |
| Polyoxy ethylene sorbitan monostearate | 25° C. | ~15 | 33.3 < S < 50 |
| Polyoxy ethylene sorbitan monooleate | 25° C. | ~15 | 12.5 < S < 14.3 |
| Triethanolamine | 25° C. | / | S < 10 |
| Polyethylene glyco-40 hydrogenated castor oil | 50° C. | ~14 | 22.2 < S < 28.6 |
| Lauroyl polyoxyl-32 glycerides | 50° C. | ~14 | S < 10 |
| d-a-tocopheryl polyethylene glycol 1000 succinate | 50° C. | ~14 | S < 10 |
| Poly-oxyethylene esters of 12-hydroxystearic acid | 50° C. | ~14 | 40 < S < 100 |
| 20% Poloxamer 188 water | 25° C. | / | S < 5 |

-continued

| Vehicle | Temp. | HLB | Approximate Solubility (mg/mL) |
|---|---|---|---|
| 20% Sulfobutylether-β-cyclodextrin in water | 25° C. | / | 10 < S < 16.7 |
| 20% 2-Hydroxypropyl-β-cyclodextrin in water | 25° C. | / | 10 < S < 16.7 |
| 20% Sulfobutylether-β-cyclodextrin in pH 4 sodium citrate buffer | 25° C. | / | 5 < S < 10 |
| 20% 2-Hydroxypropyl-β-cyclodextrin in pH 4 sodium citrate buffer | 25° C. | / | 10 < S < 16.7 |
| 25 mM sodium citrate buffer solution (pH = 4) | 25° C. | / | S < 5 |
| Water | 25° C. | / | S < 5 |
| Ethanol | 25° C. | / | 40 < S < 50 |
| Glycerin | 25° C. | / | S < 10 |
| Diethylene glycol monoethyl ether | 25° C. | / | S > 200 |
| Propylene glycol | 25° C. | / | 40 < S < 66.7 |
| Polyethylene glycol 200 | 25° C. | / | 50 < S < 66.7 |
| Polyethylene glycol 300 | 25° C. | / | 40 < S < 66.7 |
| Polyethylene glycol 400 | 25° C. | / | 40 < S < 66.7 |
| Dimethyl sulfoxide | 25° C. | / | 100 < S < 200 |
| N-methyl-2-pyrrolidone | 25° C. | / | S > 200 |
| Dimethyl acetamide | 25° C. | / | 66.7 < S < 100 |
| Dimethyl formamide | 25° C. | / | 100 < S < 200 |
| Polyethylene glycol 1500 | 70° C. | / | 50 < S < 100 |
| Polyethylene glycol 3350 | 70° C. | / | 25 < S < 50 |
| Polyethylene glycol 6000 | 70° C. | / | 25 < S < 50 |
| Glyceryl monostearate | 70° C. | / | 25 < S < 50 |
| White wax | 70° C. | / | S < 5 |
| White vaseline | 70° C. | / | S < 5 |
| Beeswax polyethylene glycol-8 | 70° C. | / | 15.7 < S < 25 |
| Glyceryl mono and di stearate | 70° C. | / | 25 < S < 50 |
| Paraffin | 70° C. | / | S < 5 |
| Ethylene glycol palmitostearate | 70° C. | 9.5 | 50 < S < 100 |
| Lanolin | 70° C. | / | S < 5 |

Ointment

EXAMPLE 2

Formulation of Solution Ointment (S01 to SO20)

| Composition | SO1 | SO2 | SO3 | SO4 | SO5 | SO6 | SO7 |
|---|---|---|---|---|---|---|---|
| Zileuton | 5.0% | 5.0% | 5.0% | 5.0% | 5.0% | 5.0% | 5.0% |
| Corn oil | | | 34.0% | | | | |
| Propylene glycol dicaprylate | | | 20.0% | | | | |
| Glyceryl monocaprate type I | | | | | 54.0% | | |
| Propylene glycol monocaprylate type II | | | | | | 40.0% | |
| Caprylocaproyl polyoxyl glycerides | | | | | | | 44.0% |
| Diethylene glycol monoethyl ether | | | 20.0% | 20.0% | 20.0% | 10.0% | 10.0% |
| Polyethylene glycol 200 | | 44.0% | | | | | |
| Polyethylene glycol 400 | 44.0% | | | | | | |
| Stearyl alcohol | | | | 10.0% | 14.0% | 10.0% | 14.0% | 10.0% |
| Polyethylene glycol 3350 | 50.0% | | | | | | |
| Polyethylene glycol 6000 | | 50.0% | | | | | |
| White vaseline | | | 10.0% | 10.0% | 10.0% | 10.0% | 10.0% |
| Sorbitan monolaurate | | | | | | 20.0% | |
| Sorbitane monooleate | | | | | | | 20.0% |
| Propylene glycol monolaurate | | | | | 50.0% | | |
| polyvinyl caprolactam-polyvinyl acetate-polyethylene glycol graft copolymer | 1.0% | 1.0% | 1.0% | 1.0% | 1.0% | 1.0% | 1.0% |
| Total weight (mg) | 100.0% | 100.0% | 100.0% | 100.0% | 100.0% | 100.0% | 100.0% |

-continued

| Composition | SO8 | SO9 | SO10 | SO11 | SO12 | SO13 | SO14 |
|---|---|---|---|---|---|---|---|
| Zileuton | 5.0% | 5.0% | 5.0% | 5.0% | 5.0% | 5.0% | 5.0% |
| Castor oil | | | 15.0% | | | | |
| Linoleoyl polyoxyl-6 glycerides | 15.0% | | | | | | |
| Medium chain triglycerides | | 15.0% | | | | | |
| Glyceryl monocaprate type I | | | | | | | 40.0% |
| Caprylocaproyl polyoxyl glycerides | | | 30.0% | | | | |
| Caprylic Glycerides | 44.0% | | | | | | |
| Diethylene glycol monoethyl ether | 10.0% | 10.0% | 10.0% | | | | 25.0% |
| Polyethylene glycol 200 | | | | | | 50.0% | |
| Polyethylene glycol 300 | | | | 29.0% | 29.0% | | |
| N-methyl-2-pyrrolidone | 5.0% | | | | | | |
| Dimethyl formamide | | 5.0% | | | | | |
| Dimethyl acetamide | | | 10.0% | | | | |
| Hexylene glycol | | 40.0% | | | | | |
| Stearyl alcohol | 10.0% | 14.0% | | | | | 19.0% |
| Beeswax polyethylene glycol-8 | | | 15.0% | | | | |
| Polyethylene glycol 1500 | | | | 40.0% | 45.0% | | |
| Polyethylene glycol 6000 | | | | 25.0% | | 44.0% | |
| Polyethylene glycol 8000 | | | | | 20.0% | | |
| White vaseline | 10.0% | 10.0% | 14.0% | | | | 10.0% |
| polyvinyl caprolactam-polyvinyl acetate-polyethylene glycol graft copolymer | 1.0% | 1.0% | 1.0% | 1.0% | 1.0% | 1.0% | 1.0% |
| Total weight (mg) | 100.0% | 100.0% | 100.0% | 100.0% | 100.0% | 100.0% | 100.0% |

| Composition | SO15 | SO16 | SO17 | SO18 | SO19 |
|---|---|---|---|---|---|
| Zileuton | 5.0% | 5.0% | 5.0% | 5.0% | 5.0% |
| Medium chain triglycerides | | | 20.0% | | |
| Oleic acid | | 20.0% | | | |
| Ethyl oleate | 20.0% | | | | |
| Liquid paraffin | | | | | 20.0% |
| Isopropyl myristate | | | | | |
| Diethylene glycol monoethyl ether | 20.0% | 25.0% | 25.0% | 25.0% | 25.0% |
| Propylene glycol | | | | | |
| Dimethyl sulfoxide | 5.0% | | | | |
| Polyacrylic acid | | | | | |
| Glyceryl mono and di stearate | | | | 19.0% | |
| Stearic acid | | | | | 9.0% |
| Cetyl alcohol | | 19.0% | | | |
| Mono and diglycerides | | | 19.0% | | |
| Paraffin | | | | | 10.0% |
| Lanolin | 30.0% | | | | |
| White vaseline | | 30.0% | 30.0% | 30.0% | 30.0% |
| Ethylene glycol palmitostearate | 19.0% | | | | |
| Propylene glycol monolaurate | | | | 20.0% | |
| polyvinyl caprolactam-polyvinyl acetate-polyethylene glycol graft copolymer | 1.0% | 1.0% | 1.0% | 1.0% | 1.0% |
| Total weight (mg) | 100.0% | 100.0% | 100.0% | 100.0% | 100.0% |

Process of Formulation Preparation for Solution Ointment (SO1 to SO19)

| Formulation | Process |
|---|---|
| SO1 to SO7, SO8 to SO10 | Step 1: Weigh all excipients except some polar solvent and add into 4 mL vial. And then melt all the excipients at 70° C./1000 rpm until getting a homogeneous solution. Step 2: Weigh 100 mg of Zileuton and add into a 2 mL vial and then add the solvent of formulation to dissolve/dispense it. Step 3: Transfer Step 2 solution to Step 1 and stir for 30 min at ~70° C./1000 rpm. Step 4: Cool down to room temperature. |
| SO11 to SO13 | Step 1: Weigh all excipients and add into 4 ml vial. And melt them at 70° C./1000 rpm until getting a homogeneous solution and then cool down to 60° C. Step 2: Weigh 100 mg of Zileuton and add into the 4 mL vial and then stir for 30 min until getting a homogeneous solution. Step 3: Transfer Step 2 solution to Step 1 and stir for 30 min ~60° C./1000 rpm. Step 4: Cool down to room temperature. |
| SO14 to SO19 | Step 1: Weigh all excipients and add into 4 ml vial. And melt them at 70° C./1000 rpm until getting a homogeneous solution and then cool down to 50° C. Step 2: Weigh 100 mg of Zileuton and add into the 4 ml vial and then stir for 30 min until getting a homogeneous solution. Step 3: Transfer Step 2 solution to Step 1 and stir for 30 min ~50° C./1000 rpm. Step 4: Cool down to room temperature. |

EXAMPLE 3

Formulation of Suspension Ointment (SPO1 to SPO17)

| Composition | SPO1 | SPO2 | SPO3 | SPO4 | SPO5 | SPO6 | SPO7 |
|---|---|---|---|---|---|---|---|
| Ziluton | 5.0% | 5.0% | 5.0% | 5.0% | 5.0% | 5.0% | 5.0% |
| Castor oil | 40.0% | | | | | | |
| Oleic acid | | 40.0% | | | | | |
| Linoleoyl polyoxyl-6 glycerides | | | 40.0% | | | | |
| Medium chain triglycerides | | | | 40.0% | | | 40.0% |
| Ethyl oleate | | | | | 40.0% | | |
| Propylene glycol dicaprylate | | | | | | 40.0% | |
| Cetyl alcohol | | | 10.0% | | | | |
| Stearyl alcohol | | 10.0% | | | | | |
| Paraffin | | | | | 10.0% | | |
| Beeswax polyethylene glycol-8 | | | | | | 10.0% | |
| White wax | | | | | | | 10.0% |
| Lanolin | 15.0% | | | | | | |
| White vaseline | 40.0% | 45.0% | 45.0% | 45.0% | 45.0% | 45.0% | 45.0% |
| Ethylene glycol palmitostearate | | | | 10.0% | | | |
| Total weight (mg) | 100.0% | 100.0% | 100.0% | 100.0% | 100.0% | 100.0% | 100.0% |

| Composition | SPO8 | SPO9 | SPO10 | SPO11 | SPO12 | SPO13 | SPO14 |
|---|---|---|---|---|---|---|---|
| Zileuton | 5.0% | 5.0% | 5.0% | 5.0% | 5.0% | 5.0% | 5.0% |
| Castor oil | | | | | | | 40.0% |
| Medium chain triglycerides | 40.0% | | | | 40.0% | | |
| Glyceryl monolinoleate | | 40.0% | | | | | |
| Liquid paraffin | | | 40.0% | | | | |
| Peceol | | | | 40.0% | | | |
| Isopropyl myristate | | | | | | 40.0% | |
| Polyacrylic acid | | | | 10.0% | | | |
| Cetyl alcohol | | | | | | | 10.0% |
| Paraffin | | | | | 10.0% | 10.0% | |
| Mono and diglycerides | 10.0% | | | | | | |
| Stearic acid | | 10.0% | | | | | |
| Glyceryl mono and di stearate | | | 10.0% | | | | |
| Lanolin | | | | | | | 45.0% |
| White vaseline | 45.0% | 45.0% | 45.0% | 45.0% | 45.0% | 45.0% | |
| Total weight (mg) | 100.0% | 100.0% | 100.0% | 100.0% | 100.0% | 100.0% | 100.0% |

| Composition | SPO15 | SPO16 | SPO17 |
|---|---|---|---|
| Zileuton | 5.0% | 5.0% | 5.0% |
| Olive Oil | 40.0% | | |
| Oleoyl polyoxyl-6 glycerides | | 40.0% | |
| Lauroyl polyoxyl-6 glycerides | | | 30.0% |
| Glyceryl monocaprate type I | | | 20.0% |
| Stearyl alcohol | 10.0% | 10.0% | |
| Paraffin | | | |
| Mono and diglycerides | | | |
| Glyceryl mono and di stearate | | | |
| Lanolin | 45.0% | | |
| White vaseline | | 45.0% | 45.0% |
| Sorbitan monolaurate | | | |
| Sorbitane monooleate | | | |
| Propylene glycol monolaurate | | | |
| Total weight (mg) | 100.0% | 100.0% | 100.0% |

Process of Formulation Preparation for Suspension Ointment (SPO1 to SPO17)

| Formulation | Process |
|---|---|
| SPO1 to SPO13 | Step 1: Mill Zileuton using mortar into ~10 micrometer of particle size observed by polarized light microscope (PLM). Step 2: Weigh all excipients and add into 4 mL vial. And then melt all the excipients at 70° C./1000 rpm until getting a homogeneous solution. Step 3: Weigh 100 mg of milled Zileuton into the 4 mL vial and then stir 15 min at ~70° C./ |

-continued

| Formulation | Process |
|---|---|
| | 1000 rpm. Step 4: Transfer Step 3 solution to Step 2 and stir for 30 min at ~70° C./1000 rpm. Step 5: Cool down to room temperature. |
| SPO14 to SPO17 | Step 1: Mill Zileuton using mortar into ~10 micrometer of particle size observed by PLM. Step 2: Weigh all excipients and add into 4 mL vial. And melt all the excipients at 70° C./ 1000 rpm until getting a homogeneous solution and then cool down to 50° C. Step 3: Weigh 100 mg of milled Zileuton into |

-continued

| Formulation | Process |
|---|---|
| | the 4 mL vial and then stir 30 min at ~50° C./ 1000 rpm.<br>Step 4: Transfer Step 3 solution to Step 2 and stir for 30 min at ~50° C./1000 rpm.<br>Step 5: Cool down to room temperature. |

Cream

EXAMPLE 4

Formulation of Solution Cream (SC1 to SC20)

| Composition | SC1 | SC2 | SC3 | SC4 | SC5 | SC6 | SC7 |
|---|---|---|---|---|---|---|---|
| Zileuton | 5.0% | 5.0% | 5.0% | 5.0% | 5.0% | 5.0% | 5.0% |
| Corn oil | | | | | | 20.0% | |
| Linoleoyl polyoxyl-6 glycerides | | | | | | | 20.0% |
| Glyceryl monocaprate type I | | 20.0% | | | | | |
| Propylene glycol monocaprylate type II | | | 20.0% | | | | |
| Caprylocaproyl polyoxyl glycerides | | | | 20.0% | | | |
| Caprylic glyceride | 24.0% | | | | | | |
| Ethanol | | 20.0% | | | | | |
| Diethylene glycol monoethyl ether | 25.0% | | 20.0% | | 9.0% | 14.0% | 20.0% |
| N-methyl-2-pyrrolidone | | | | 10.0% | | | |
| Dimethyl formamide | | | | | 10.0% | | |
| Dimethyl acetamide | | | | | | 10.0% | |
| Hexylene glycol | | | | | 20.0% | | |
| Cetyl alcohol | | 24.0% | | 25.0% | | | |
| Stearyl alcohol | | | 20.0% | | 20.0% | | |
| Beeswax polyethylene glycol-8 | | 20.0% | | | | 20.0% | 14.0% |
| Lanolin | | | | 25.0% | 25.0% | | 30.0% |
| White vaseline | 10.0% | | 25.0% | | | 20.0% | |
| Ethylene glycol palmitostearate | 15.0% | | | | | | |
| Caprylocaproyl polyoxyl glycerides | | | 9.0% | | | | 10.0% |
| Polyoxyl 35 hydrogenated castor oil | | | | 14.0% | | | |
| Polyethylene glycol-40 hydrogenated castor oil | | | | | 10.0% | | |
| Sodium lauryl sulfate | | | | | | 10.0% | |
| d-a-tocopheryl polyethylene glycol 1000 succinate | | 10.0% | | | | | |
| Propylene glycol monolaurate | 20.0% | | | | | | |
| Polyvinyl caprolactam-polyvinyl acetate-polyethylene glycol graft copolymer | 1.0% | 1.0% | 1.0% | 1.0% | 1.0% | 1.0% | 1.0% |
| Total weight (mg) | 100.0% | 100.0% | 100.0% | 100.0% | 100.0% | 100.0% | 100.0% |

| Composition | SC8 | SC9 | SC10 | SC11 | SC12 | SC13 | SC14 |
|---|---|---|---|---|---|---|---|
| Zileuton | 5.0% | 5.0% | 5.0% | 5.0% | 5.0% | 5.0% | 5.0% |
| Medium chain triglycerides | 20.0% | | 10.0% | | | 20.0% | |
| Ethyl oleate | | | | | | | 20.0% |
| Propylene glycol dicaprylate | | 20.0% | | | | | |
| Caprylic glyceride | | | | | 20.0% | | |
| Diethylene glycol monoethyl ether | | 25.0% | 25.0% | 20.0% | | | |
| Propylene glycol | | | | | 20.0% | | |
| Polyethylene glycol 200 | | | | | | 30.0% | |
| Polyethylene glycol 300 | | | | | | | 30.0% |
| Polyethylene glycol 400 | 30.0% | | | | | | |
| Mono and diglycerides | | 9.0% | 14.0% | | | | |
| Glyceryl mono and di stearate | | | | 14.0% | 14.0% | | |
| Polyethylene glycol 3350 | 14.0% | | | | | 14.0% | 14.0% |
| Ethylene glycol palmitostearate | 20.0% | 20.0% | 15.0% | 20.0% | 30.0% | 20.0% | 20.0% |
| Sorbitan monolaurate | | | 10.0% | | | | |
| Sorbitane monooleate | | | | 20.0% | | | |
| Polyethylene glycol sorbitan monolaurate | | 20.0% | | | | | |
| Polyoxyethylene sorbitan monooleate | | | 20.0% | | | | |
| d-a-tocopheryl polyethylene glycol 1000 succinate | | | | 20.0% | | | |
| Triethanolamine | 10.0% | | | | | 10.0% | |
| Lecithin from egg | | | | | 10.0% | | |
| Poly-oxyethylene esters of 12-hydroxystearic acid | | | | | | | 10.0% |
| Polyvinyl caprolactam-polyvinyl acetate-polyethylene glycol graft copolymer | 1.0% | 1.0% | 1.0% | 1.0% | 1.0% | 1.0% | 1.0% |
| Total weight (mg) | 100.0% | 100.0% | 100.0% | 100.0% | 100.0% | 100.0% | 100.0% |

US 12,582,598 B2

17                                                                                      18

-continued

| Composition | SC15 | SC16 | SC17 | SC18 | SC19 | SC20 |
|---|---|---|---|---|---|---|
| Zileuton | 5.0% | 5.0% | 5.0% | 5.0% | 5.0% | 5.0% |
| Medium chain triglycerides | 20.0% | | | 20.0% | | |
| Glyceryl monolinoleate | | 20.0% | | | | |
| Peceol | | | 20.0% | | | |
| Isopropyl myristate | | | | | 20.0% | |
| Ethanol | | | | 30.0% | | |
| Diethylene glycol monoethyl ether | 20.0% | 30.0% | 30.0% | | 20.0% | 30.0% |
| Beeswax polyethylene glycol-8 | | | | 14.0% | | |
| White wax | | | 14.0% | 14.0% | | |
| Stearic acid | | | | | 15.0% | |
| Glyceryl mono and di stearate | | | | | | 20.0% |
| Polyethylene glycol 1500 | 10.0% | | | | | |
| Polyethylene glycol 6000 | 10.0% | | | | | |
| Lanolin | | | | | 20.0% | 34.0% |
| White vaseline | | 20.0% | 20.0% | | | |
| Ethylene glycol palmitostearate | 24.0% | | | 20.0% | | |
| Sorbitan monolaurate | | | | | 9.0% | |
| Polyethylene glycol octadecyl ether | | | | | | 10.0% |
| Polyoxy ethylene sorbitan monooleate | | | | 10.0% | | |
| d-a-tocopheryl polyethylene glycol 1000 succinate | | | 10.0% | | | |
| Lecithin from soybean | | | | | 10.0% | |
| Poloxamer 407 | 10.0% | | | | | |
| Poloxamer 188 | | 10.0% | | | | |
| Polyvinyl caprolactam-polyvinyl acetate-polyethylene glycol graft copolymer | 1.0% | 1.0% | 1.0% | 1.0% | 1.0% | 1.0% |
| Total weight (mg) | 100.0% | 100.0% | 100.0% | 100.0% | 100.0% | 100.0% |

Process of Formulation Preparation for Solution Cream (SC1 to SC20)

| Formulation | Process |
|---|---|
| SC1, SC3, SC4, SC5, SC8, SC9, SC10, SC11, SC12, SC14, SC15, SC18, SC19 | Step 1: Weigh all excipients and add into 4 mL vial and then melt them at 70° C./1000 rpm until getting a homogeneous solution. Step 2: Weigh 100 mg of Zileuton and add into the 4 mL vial and then stir for 15 min at ~50° C./1000 rpm. Step 3: Transfer Step 2 solution to Step 1 and stir for 30 min at ~50° C./1000 rpm. Step 4: Cool down to room temperature. |
| SC2, SC6, SC7, SC13, SC16, SC17 | Step 1: Weigh all excipients and add into 4 mL vial and then melt them at 70° C./1000 rpm until getting a homogeneous solution. Step 2: Weigh 100 mg of Zileuton and add into the 4 mL vial and then stir for 15 min at ~70° C./1000 rpm. |

-continued

| Formulation | Process |
|---|---|
| | Step 3: Transfer Step 2 solution to Step 1 and stir for 30 min at ~70° C./1000 rpm. Step 4: Cool down to room temperature. |
| SC20 | Step 1: Weigh all excipients and add into 4 mL vial and then melt them at 70° C./1000 rpm until getting a homogeneous solution. Step 2: Weigh 100 mg of Zileuton and add into the 4 mL vial and then stir for overnight at ~50° C./1000 rpm. Step 3: Transfer Step 2 solution to Step 1 and stir for 30 min at ~50° C./1000 rpm. Step 4: Cool down to room temperature. |

EXAMPLE 5

Formulation of Suspension Cream (SPC1 to SPC20)

| Composition | SPC1 | SPC2 | SPC3 | SPC4 | SPC5 | SPC6 | SPC7 |
|---|---|---|---|---|---|---|---|
| Zileuton | 5.0% | 5.0% | 5.0% | 5.0% | 5.0% | 5.0% | 5.0% |
| Medium chain triglycerides | | | | 20.0% | | | |
| Liquid paraffin | | | | | | | 20.0% |
| Peceol | | | | | | 20.0% | |
| Caprylic glycerides | | | | | 20.0% | | |
| Isopropyl myristate | | | 20.0% | | | | |
| Glycerin | 25.0% | 25.0% | 25.0% | 25.0% | 25.0% | 25.0% | 25.0% |
| Cetyl alcohol | 20.0% | 20.0% | | | | | |
| Stearyl alcohol | | | 20.0% | | | | |
| Paraffin | | | | 20.0% | | | |
| Beeswax polyethylene glycol-8 | | | | | 20.0% | | |
| White wax | | | | | | 20.0% | |
| Mono and diglycerides | | | | | | | 20.0% |
| Lanolin | 20.0% | 20.0% | 20.0% | | | | |
| White vaseline | | | | 20.0% | 20.0% | 20.0% | 20.0% |
| Sorbitan monolaurate | | 20.0% | | | | | |
| Sorbitane monooleate | 20.0% | | | | | | |
| Polyoxyl 35 hydrogenated castor oil | 10.0% | | | | | | |

-continued

| | | | | | | | |
|---|---|---|---|---|---|---|---|
| Polyethylene glycol-40 hydrogenated castor oil | | 10.0% | | | | | |
| Sodium lauryl sulfate | | | 10.0% | | | | |
| Polyethylene glycol octadecyl ether | | | | 10.0% | | | |
| Lauroyl poloxyl-32 glycerides | | | | | 10.0% | | |
| Lecithin from egg | | | | | | 10.0% | |
| Polyoxy ethylene sorbitan monooleate | | | | | | | 10.0% |
| Total weight (mg) | 100.0% | 100.0% | 100.0% | 100.0% | 100.0% | 100.0% | 100.0% |

| Composition | SPC8 | SPC9 | SPC10 | SPC11 | SPC12 | SPC13 | SPC14 |
|---|---|---|---|---|---|---|---|
| Zileuton | 5.0% | 5.0% | 5.0% | 5.0% | 5.0% | 5.0% | 5.0% |
| Medium chain triglycerides | | 20.0% | 20.0% | | | 20.0% | |
| Glyceryl monolinoleate | 20.0% | | | | | | |
| Lauroyl polyoxyl-6 glycerides | | | | | | | 20.0% |
| Ethyl oleate | | | | | 20.0% | | |
| Propylene glycol dicaprylate | | | | 20.0% | | | |
| Glycerin | 25.0% | 25.0% | 25.0% | 25.0% | 25.0% | 25.0% | 25.0% |
| Cetyl alcohol | | | | | | | 20.0% |
| Stearyl alcohol | | | | 10.0% | | | |
| Stearic acid | | | | | 20.0% | | |
| Glyceryl mono and di stearate | 20.0% | 10.0% | | | | 20.0% | |
| Lanolin | | | | | 20.0% | 20.0% | 20.0% |
| White vaseline | 20.0% | 20.0% | 20.0% | 20.0% | | | |
| Lecithin from soybean | | | 10.0% | | | | |
| Polyethylene glycol sorbitan monolaurate | | | | 10.0% | | | |
| Polyoxy ethylene sorbitan monostearate | | | | | 10.0% | | |
| d-a-tocopheryl polyethylene glycol 1000 succinate | 10.0% | | | | | | |
| 2-Hydroxypropyl-β-cyclodextrin | | | | | | | 10.0% |
| Sulfobutylether-β-cyclodextrin | | 20.0% | | | | | |
| Poloxamer 407 | | | 20.0% | | | | |
| Poly-oxyethylene esters of 12-hydroxystearic acid | | | | | | 10.0% | |
| Triethanolamine | | | | 10.0% | | | |
| Total weight (mg) | 100.0% | 100.0% | 100.0% | 100.0% | 100.0% | 100.0% | 100.0% |

| Composition | SPC15 | SPC16 | SPC17 | SPC18 | SPC19 | SPC20 |
|---|---|---|---|---|---|---|
| Zileuton | 5.0% | 5.0% | 5.0% | 5.0% | 5.0% | 5.0% |
| Castor oil | | | | | | 20.0% |
| Oleic acid | | | | | 20.0% | |
| Olive oil | | | | 20.0% | | |
| Linoleoyl polyoxyl-6 glycerides | | 20.0% | | | | |
| Oleoyl polyoxyl-6 glycerides | 20.0% | | | | | |
| Glycerin | 25.0% | 25.0% | 25.0% | 25.0% | 25.0% | 25.0% |
| Cetyl alcohol | | | | 20.0% | 20.0% | |
| Stearyl alcohol | 20.0% | | | | | |
| Paraffin | | 20.0% | | | | |
| Beeswax polyethylene glycol-8 | | | 20.0% | | | 20.0% |
| White wax | | | | 20.0% | | |
| Mono and diglycerides | | | | | 20.0% | |
| Stearic acid | | | | | | 10.0% |
| Glyceryl mono and di stearate | | | | | | 10.0% |
| Lanolin | 20.0% | | | | | |
| White vaseline | | 20.0% | 20.0% | | | |
| Lecithin from egg | | 10.0% | | | | |
| Lecithin from soybean | | | 10.0% | | | |
| d-a-tocopheryl polyethylene glycol 1000 succinate | | | | 10.0% | | |
| Poloxamer 407 | | | | | 10.0% | |
| Poloxamer 188 | 10.0% | | | | | |
| Triethanolamine | | | | | | 10.0% |
| Propylene glycol monolaurate | | | 20.0% | | | |
| Total weight (mg) | 100.0% | 100.0% | 100.0% | 100.0% | 100.0% | 100.0% |

Process of Formulation Preparation for Suspension Cream
(SPC1 to SPC20)

| Formulation | Process |
|---|---|
| SPC1 to SPC9; SPC14 | Step 1: Mill Zileuton using mortar into ~10 micrometer of particle size observed by PLM. Step 2: Weigh all excipients and add into 4 mL vial. And then melt all the excipients at 70° C./1000 rpm until getting a homogeneous solution. Step 3: Weigh 100 mg of milled Zileuton into the 4 mL vial and then stir 15 min at ~60° C./1000 rpm. Step 4: Transfer Step 3 solution to Step 2 and stir for 30 min at ~60° C./1000 rpm. Step 5: Cool down to room temperature. |

-continued

| Formulation | Process |
|---|---|
| SPC10 to SPC11; SPC13, SPC15, SPC16, SPC17 to SPC20 | Step 1: Mill Zileuton using mortar into ~10 micrometer of particle size observed by PLM. Step 2: Weigh all excipients and add into 4 mL vial. And then melt all the excipients at 70° C./1000 rpm until getting a homogeneous solution. Step 3: Weigh 100 mg of milled Zileuton into the 4 mL vial and then stir 15 min at ~70° C./1000 rpm. Step 4: Transfer Step 3 solution to Step 2 and stir for 30 min at ~70° C./1000 rpm. Step 5: Cool down to room temperature. |

EXAMPLE 6

Formulation of Water/Buffer solution Cream (WB1 to WB20)

| Composition | WB1 | WB2 | WB3 | WB4 | WB5 | WB6 | WB7 |
|---|---|---|---|---|---|---|---|
| Zileuton | 5.0% | 5.0% | 5.0% | 5.0% | 5.0% | 5.0% | 5.0% |
| Medium chain triglycerides | | | | | 7.5% | | |
| Propylene glycol dicaprylate | | | | 15.0% | | | |
| Glyceryl monocaprate type I | | 20.0% | | | | | |
| Propylene glycol monocaprylate type II | 20.0% | | | | | | |
| Caprylic glycerides | | | | | | | 15.0% |
| Diethylene glycol monoethyl ether | 20.0% | 20.0% | 9.0% | 25.0% | 25.0% | 20.0% | |
| Propylene glycol | | | | | | | 20.0% |
| Dimethyl formamide | | | 10.0% | | | | |
| Hexylene glycol | | | 15.0% | | | | |
| Cetyl alcohol | | 20.0% | | | | | |
| Stearyl alcohol | 20.0% | | 20.0% | | | | |
| Glyceryl mono and di stearate | | | | 9.0% | 14.0% | 14.0% | 14.0% |
| Lanolin | | | 20.0% | | | | |
| White vaseline | 20.0% | 20.0% | | | | | |
| Ethylene glycol palmitostearate | | | | 20.0% | 15.0% | 20.0% | 30.0% |
| Sorbitan monolaurate | | | | | 7.5% | | |
| Sorbitane monooleate | | | | | | 15.0% | |
| Caprylocaproyl polyoxyl glycerides | 9.0% | 9.0% | | | | | |
| Polyethylene glycol-40 hydrogenated castor oil | | | 10.0% | | | | |
| Lecithin from egg | | | | | | | 10.0% |
| Polyethylene glycol sorbitan monolaurate | | | | 20.0% | | | |
| Polyoxy ethylene sorbitan monooleate | | | | | 20.0% | | |
| d-a-tocopheryl polyethylene glycol 1000 succinate | | | | | | 20.0% | |
| Pure water | 6.0% | | | | | | 6.0% |
| Acid Phthalate buffer (pH4.0) | | 6.0% | | | | | |
| Acetate buffer (pH 4.1) | | | 11.0% | | | | |
| Citrate buffer (pH4.0) | | | | 6.0% | | | |
| Phosphate buffer (pH6.0) | | | | | 6.0% | | |
| Merck buffer pH4.0 | | | | | | 6.0% | |
| Total weight (mg) | 100.0% | 100.0% | 100.0% | 100.0% | 100.0% | 100.0% | 100.0% |

| Composition | WB8 | WB9 | WB10 | WB11 | WB12 | WB13 | WB14 |
|---|---|---|---|---|---|---|---|
| Zileuton | 5.0% | 5.0% | 5.0% | 5.0% | 5.0% | 5.0% | 5.0% |
| Medium chain triglycerides | 15.0% | | 15.0% | | 15.0% | | |
| Ethyl oleate | | 15.0% | | | | | |
| Glyceryl monocaprate type I | | | | | | 15.0% | |
| Caprylocaproyl polyoxyl glycerides | | | | | | | 15.0% |
| Glyceryl monolinoleate | | | | 15.0% | | | |
| Ethanol | | | | | | 30.0% | 20.0% |
| Diethylene glycol monoethyl ether | | | 20.0% | 30.0% | | | |
| Polyethylene glycol 200 | 30.0% | | | | | | |
| Polyethylene glycol 300 | | 30.0% | | | | | |
| N-methyl-2-pyrrolidone | | | | | | | 10.0% |
| White wax | | | | 14.0% | | | |
| Beeswax polyethylene glycol-8 | | | | | 14.0% | 20.0% | |
| Cetyl alcohol | | | | | | 24.0% | 25.0% |
| Polyethylene glycol 1500 | | | 10.0% | | | | |
| Polyethylene glycol 3350 | 14.0% | 14.0% | | | | | |
| Polyethylene glycol 6000 | | | 10.0% | | | | |

-continued

| Composition | | | | | | | |
|---|---|---|---|---|---|---|---|
| Lanolin | | | | | | | 25.0% |
| White vaseline | | | | 20.0% | | | |
| Ethylene glycol palmitostearate | 20.0% | 20.0% | 24.0% | | 20.0% | | |
| Polyoxyl 35 hydrogenated castor oil | | | | | | | 14.0% |
| Polyoxy ethylene sorbitan monooleate | | | | | 10.0% | | |
| d-a-tocopheryl polyethylene glycol 1000 succinate | | | | | | 10.0% | |
| Poly-oxyethylene esters of 12-hydroxystearic acid | | 10.0% | | | | | |
| Poloxamer 407 | | | 10.0% | | | | |
| Triethanolamine | 10.0% | | | 10.0% | | | |
| Pure water | | | | | | | 6.0% |
| Acid phthalate buffer (pH4.0) | 6.0% | 6.0% | | | | | |
| Acetate buffer (pH 4.1) | | | 6.0% | | | | |
| Citrate buffer (pH4.0) | | | | 6.0% | | | |
| Phosphate buffer (pH6.0) | | | | | 6.0% | | |
| Merck buffer pH4.0 | | | | | | 6.0% | |
| Total weight (mg) | 100.0% | 100.0% | 100.0% | 100.0% | 100.0% | 100.0% | 100.0% |

| Composition | WB15 | WB16 | WB17 | WB18 | WB19 | WB20 |
|---|---|---|---|---|---|---|
| Zileuton | 5.0% | 5.0% | 5.0% | 5.0% | 5.0% | 5.0% |
| Medium chain triglycerides | | | 15.0% | | | |
| Caprylocaproyl polyoxyl glycerides | | 10.0% | | 15.0% | | |
| Corn oil | 15.0% | | | | | |
| Linoleoyl polyoxyl-6 glycerides | | 15.0% | | | | |
| Diethylene glycol monoethyl ether | 14.0% | 20.0% | | | 15.0% | |
| Polyethylene glycol 400 | | | 30.0% | | | |
| Dimethyl acetamide | 10.0% | | | | | |
| Hexylene glycol | | | | | 15.0% | |
| Beeswax polyethylene glycol-8 | 20.0% | 14.0% | | | | |
| Cetyl alcohol | | | | | | 25.0% |
| Polyethylene glycol 3350 | | | 14.0% | | | |
| Lanolin | | 30.0% | | 9.0% | | |
| White vaseline | 20.0% | | | | | |
| Ethylene glycol palmitostearate | | | 20.0% | 15.0% | 50.0% | 50.0% |
| Poly-oxyethylene esters of 12-hydroxystearic acid | | | | 50.0% | | |
| Triethanolamine | | | 10.0% | | | |
| Sodium lauryl sulfate | 10.0% | | | | | |
| Lauroyl polyoxyl-32 glycerides | | | | | 5.0% | |
| Acid phthalate buffer (pH4.0) | 6.0% | | | | | |
| Acetate buffer (pH 4.1) | | 6.0% | | | | |
| Citrate buffer (pH4.0) | | | 6.0% | | | |
| Phosphate buffer (pH6.0) | | | | 6.0% | | |
| Merck buffer pH4.0 | | | | | 10.0% | 20.0% |
| Total weight (mg) | 100.0% | 100.0% | 100.0% | 100.0% | 100.0% | 100.0% |

Process of Formulation Preparation for Water/Buffer solution Cream (WB1 to WB20)

| Formulation | Process |
|---|---|
| WB1 to WB20 | Step1: Weight all excipients (except Zileuton and water/buffer) and add into a 4 mL vial. Step 2: Stir all the excipient at 70° C./1500 rpm until getting a homogeneous solution and then cool it to 50-60° C. Step3: Weight Zileuton and water/buffer and add to Step 2 vial and stir at 1500 rpm until |

-continued

| Formulation | Process |
|---|---|
| | getting a homogeneous solution. Step 4: Cool down to room temperature. |

Gel

EXAMPLE 7

Formulation of Gel (Gel-1 to Gel-20)

| Composition | Gel-1 | Gel-2 | Gel-3 | Gel-4 | Gel-5 | Gel-6 | Gel-7 |
|---|---|---|---|---|---|---|---|
| Zileuton | 5.0% | 5.0% | 5.0% | 5.0% | 5.0% | 5.0% | 5.0% |
| Ethanol | 80.0% | | | | | | |
| Diethylene glycol monoethyl ether | | 75.0% | | | | | 57.0% |
| Propylene glycol | | | 80.0% | | | | |
| Polyethylene glycol 200 | | | | 80.0% | | | |
| Polyethylene glycol 300 | | | | | 80.0% | | |
| Polyethylene glycol 400 | | | | | | 80.0% | |
| N-methyl-2-pyrrolidone | | | | | | | 5.0% |

-continued

| | | | | | | | |
|---|---|---|---|---|---|---|---|
| Acrylic acid polymer | 5.0% | 5.0% | 5.0% | 5.0% | 5.0% | 5.0% | 8.0% |
| Triethanolamine | | | | | | | 5.0% |
| Pure water | 10.0% | 15.0% | 10.0% | 10.0% | 10.0% | | |
| 0.01N HCl (pH 2.0) | | | | | | | 20.0% |
| Phosphate buffer (pH 7.5) | | | | | | 10.0% | |
| | | | | | | | |
| Total weight (mg) | 100.0% | 100.0% | 100.0% | 100.0% | 100.0% | 100.0% | 100.0% |

| Composition | Gel-8 | Gel-9 | Gel-10 | Gel-11 | Gel-12 | Gel-13 | Gel-14 |
|---|---|---|---|---|---|---|---|
| Zileuton | 5.0% | 5.0% | 5.0% | 5.0% | 5.0% | 5.0% | 5.0% |
| Diethylene glycol monoethyl ether | | | 55.0% | 55.0% | 55.0% | 55.0% | 55.0% |
| Propylene glycol | 57.0% | | | | | | |
| Polyethylene glycol 400 | 57.0% | | | | | | |
| Dimethyl formamid | 5.0% | | | | | | |
| Dimethyl acetamide | | 5.0% | | | | | |
| Acrylic acid polymer | 8.0% | 8.0% | 3.0% | 5.0% | 5.0% | 5.0% | 5.0% |
| Poly-oxyethylene esters of 12-hydroxystearic acid | | | 20.0% | | | | |
| Triethanolamine | 5.0% | 5.0% | | | | | |
| Caprylocaproyl polyoxy lglycerides | | | | | | 20.0% | |
| Polyethylene glycol-40 hydrogenated castor oil | | | | | | | 20.0% |
| Polyoxy ethylene sorbitan monooleate | | | | | | 20.0% | |
| d-a-tocopheryl polyethylene glycol 1000 succinate | | | | | 20.0% | | |
| Pure water | | | 17.0% | 15.0% | 15.0% | 15.0% | 15.0% |
| Sodium citrate buffer (pH 4.0) | 20.0% | | | | | | |
| Phosphate buffer (pH 6.0) | | 20.0% | | | | | |
| | | | | | | | |
| Total weight (mg) | 100.0% | 100.0% | 100.0% | 100.0% | 100.0% | 100.0% | 100.0% |

| Composition | Gel-15 | Gel-16 | Gel-17 | Gel-18 | Gel-19 | Gel-20 |
|---|---|---|---|---|---|---|
| Zileuton | 5.0% | 5.0% | 5.0% | 5.0% | 5.0% | 5.0% |
| Diethylene glycol monoethyl ether | | | 50.0% | 50.0% | | |
| Propylene glycol | 25.0% | | | | | |
| Polyethylene glycol 200 | | 25.0% | | | | |
| Methylcellulose 400 cP | 10.0% | | | | | |
| Methylcellulose 4000 cP | | 10.0% | | | | |
| Hydroxy propyl methyl cellulose K4M | | | 5.0% | | | |
| Hydroxy propyl methyl cellulose K15M | | | | 10.0% | | |
| Sodium carboxymethyl cellulose | | | | | 20.0% | |
| Gum acacia | | | | | | 30.0% |
| Caprylocaproyl polyoxyl glycerides | | | | | 20.0% | |
| Polyoxyl 35 hydrogenated castor oil | | | | | | 20.0% |
| Pure water | 60.0% | | | | | 45.0% |
| 0.01N HCl (pH 2.0) | | 60.0% | | | | |
| Sodium citrate buffer (pH 4.0) | | | 40.0% | | | |
| Phosphate buffer (pH 6.0) | | | | 35.0% | | |
| Phosphate buffer (pH 7.5) | | | | | 55.0% | |
| | | | | | | |
| Total weight (mg) | 100.0% | 100.0% | 100.0% | 100.0% | 100.0% | 100.0% |

Process of Formulation Preparation for Gel (Gel-1 to Gel-20)

| Formulation | Process |
|---|---|
| Gel-1 to Gel-14 | Step 1: Weight Zileuton, solvent and surfactant and add into 4 mL vail<br>Step 2: Vortex and sonicate until Zileuton is fully dissolved at room temperature.<br>Step 3: Add gel material and water/buffer solution to Step 2 and then stir manually for 15 min at room temperature. |
| Gel-15 to Gel 20 | Step 1: Weight Zileuton, solvent and surfactant and add into 4 mL vail |

-continued

| Formulation | Process |
|---|---|
| | Step 2: Vortex and sonicate until getting a homogeneous solution.<br>Step 3: Add gel material and water/buffer solution to Step 2 and then stir manually for 15 min at room temperature. |

Lotion

EXAMPLE 8

Formulation of Lotion (LO1 to LO20)

| Composition | LO1 | LO2 | LO3 | LO4 | LO5 | LO6 | LO7 |
|---|---|---|---|---|---|---|---|
| Zileuton | 5.0% | 5.0% | 5.0% | 5.0% | 5.0% | 5.0% | 5.0% |
| Diethylene glycol monoethyl ether | 75.0% | 25.0% | 50.0% | | | | 10.0% |

-continued

| Component | | | | | | | |
|---|---|---|---|---|---|---|---|
| Propylene glycol | | | | 45.0% | | | |
| Polyethylene glycol 200 | | | | | 45.0% | | |
| Polyethylene glycol 300 | | | | | | 45.0% | |
| Polyethylene glycol 400 | | | | | | | 45.0% |
| N-methyl-2-pyrrolidone | | | | 5.0% | | | |
| Dimethyl formamide | | | | | 5.0% | | |
| Dimethyl acetamide | | | | | | 5.0% | |
| Caprylocaproyl polyoxyl glycerides | | 50.0% | 25.0% | | | | |
| Poly-oxyethylene esters of 12-hydroxystearic acid | | | | 25.0% | | | |
| Polyoxy ethylene sorbitan monooleate | | | | | | 25.0% | |
| d-a-tocopheryl polyethylene glycol 1000 succinate | | | | | | | 25.0% |
| Triethanolamine | | | | | 25.0% | | |
| Pure water | 20.0% | | | | | | 15.0% |
| Acid phthalate buffer (pH4.0) | | 20.0% | | | | | |
| Acetate buffer (pH 4.1) | | | 20.0% | | | | |
| Citrate buffer (pH4.0) | | | | 20.0% | | | |
| Phosphate buffer (pH6.0) | | | | | 20.0% | | |
| Merck buffer pH4.0 | | | | | | 20.0% | |
| Total weight (mg) | 100.0% | 100.0% | 100.0% | 100.0% | 100.0% | 100.0% | 100.0% |

| Composition | LO8 | LO9 | LO10 | LO11 | LO12 | LO13 | LO14 |
|---|---|---|---|---|---|---|---|
| Zileuton | 5.0% | 5.0% | 5.0% | 5.0% | 5.0% | 5.0% | 5.0% |
| Caprylocaproyl polyoxyl glycerides | | | | | | 10.0% | 50.0% |
| Ethanol | 45.0% | 50.0% | | | | | |
| Diethylene glycol monoethyl ether | | 10.0% | 10.0% | 10.0% | 10.0% | 20.0% | |
| Propylene glycol | | | 50.0% | | | | |
| Hexylene glycol | | | | | | | 10.0% |
| Polyethylene glycol 200 | | | | 50.0% | | | |
| Polyethylene glycol 300 | | | | | 50.0% | | |
| Polyethylene glycol 1500 | | | | | | | 20.0% |
| Sodium lauryl sulfate | | | 20.0% | | | | |
| Polyethylene glycol octadecyl ether | | 20.0% | | | | | |
| Lecithin from soybean | 25.0% | | | | | | |
| Polyoxyl 35 hydrogenated castor oil | | | | | 20.0% | | |
| Polyethylene glycol-40 hydrogenated castor oil | | | | 20.0% | | | |
| Poly-oxyethylene esters of 12-hydroxystearic acid | | | | | | 50.0% | |
| Pure water | | | | | | 15.0% | |
| Acid phthalate buffer (pH4.0) | 15.0% | | | | | | 15.0% |
| Acetate buffer (pH 4.1) | | 15.0% | | | | | |
| Citrate buffer (pH4.0) | | | 15.0% | | | | |
| Phosphate buffer (pH6.0) | | | | 15.0% | | | |
| Merck buffer pH4.0 | | | | | 15.0% | | |
| Total weight (mg) | 100.0% | 100.0% | 100.0% | 100.0% | 100.0% | 100.0% | 100.0% |

| Composition | LO15 | LO16 | LO17 | LO18 | LO19 | LO20 |
|---|---|---|---|---|---|---|
| Zileuton | 5.0% | 5.0% | 5.0% | 5.0% | 5.0% | 5.0% |
| Glyceryl monocaprate Type I | | 10.0% | | | | |
| Propylene glycol monocaprylate type II | 10.0% | | | | | |
| Ethanol | | 15.0% | 15.0% | | | |
| Polyethylene glycol 200 | | | | | 30.0% | |
| Polyethylene glycol 400 | | | | 20.0% | | |
| Polyethylene glycol 1500 | | | | 55.0% | | |
| Polyethylene glycol 3350 | 20.0% | | | | 25.0% | |
| Dimethyl formamide | | | | | | 10.0% |
| Sorbitan monolaurate | | | | | | 20.0% |
| Caprylocaproyl polyoxyl glycerides | 50.0% | | | | | |
| Polyoxy ethylene sorbitan monostearate | | | | | 20.0% | |
| Poly-oxyethylene esters of 12-hydroxystearic acid | | 50.0% | 50.0% | | | 65.0% |
| Polyoxy ethylene sorbitan monooleate | | | | | | |
| Propylene glycol monolaurate | | | 10.0% | | | |
| Acetate buffer (pH 4.1) | 15.0% | | | | | |
| Citrate buffer (pH4.0) | | 20.0% | | | | |
| Phosphate buffer (pH6.0) | | | 20.0% | | | |
| Merck buffer (pH4.0) | | | | 20.0% | 20.0% | |
| Total weight (mg) | 100.0% | 100.0% | 100.0% | 100.0% | 100.0% | 100.0% |

Process of Formulation Preparation for Lotion (LO1 to LO20)

| Formulation | Process |
|---|---|
| LO1 to LO3, LO5 to LO6, LO12 | Step 1: Weigh all excipients except Zileuton and add into 4 mL vial and then melt them at 70° C./1000 rpm until getting a homogeneous solution and then cool to room temperature. Step 2: Weigh 100 mg of Zileuton and add into the 4 mL vial and then vortex and sonicate until getting homogeneous solution at room temperature. |
| LO4, LO7 to LO11, LO13 to LO20 | Step 1: Weight all excipients including Zileuton and add into 4 mL vial Step 2: Vortex and sonicate until getting homogeneous solution at room temperature. |

EXAMPLE 9

Phorbol Ester Induced Ear Edema Test

The effect of Zileuton-containing formulations on phorbol ester induced ear edema in ICR mice was evaluated. One hundred and twenty (120) female ICR mice were assigned to eleven (11) groups by randomization with BioBook software to achieve similar mean weight and right ear thickness baseline among groups. Mice were terminated by 95% $CO_2$ asphyxiation and then cervical dislocation.

Totally nine (9) Zileuton-containing formulations which are SO13, SO17, WB6, Gel-10, Gel-11, LO3, LO13, SPC19 and Zileuton 1.0% cream were selected for the tests Dexamethasone were used for the reference and Acetone was treated to the vehicle group.

Mice were anesthetized with 2-5 isoflurane. The mice were sensitized by painting 5 μg of phorbol ester dissolved in 0.02 mL of Acetone on ear inside and out. For dosing of test compounds and positive controls, animals were anesthetized with 2-5% isoflurane for about 5 minutes to ensure that the test compounds and positive controls were well given to the skin and not licking by the mice. Six (6) hours after the modeling, the both side's ear thickness were measured after anesthetized by isoflurane (2-3%), respectively. Ear swelling response was determined by ear thickness measured with a micrometer before challenge and 6 hours after challenge and reported as the mean change in ear thickness (ΔT±S.E.M.). Percent suppression of ear swelling response was calculated as % suppression=[1−(ΔT of sensitized mice exposed to experimental treatment/ΔT of sensitized mice exposed to vehicle treatment)]×100.

Results are shown in FIG. 1.

Phorbol ester (5 μg/ear) induced an edematogenic response as evidenced by a marked increase in ear thickness. As the treatment with positive control Dexamethasone showed significant decrease in ear swelling. And the test compounds which are nine (9) Zileuton-containing formulations showed good disease inhibition ration. In comparison to Zileuton 1.0% cream, 5013, WB6, Gel-10 and Gel-11 showed significant disease inhibition, especially test article 4 which is Gel-10 showed most strong disease inhibition which presented as the highest suppression rate.

TABLE

| Suppression Rate | |
|---|---|
| Group | % suppression Vs G1-right ear |
| PMA-Dex | 27.14 |
| PMA-Test article 1 SO13 | 29.15 |
| PMA-Test article 2 SO17 | 25.13 |
| PMA-Test article 3 WB6 | 32.16 |
| PMA-Test article 4 Gel-10 | 36.68 |
| PMA-Test article 5 Gel-11 | 26.63 |
| PMA-Test article 6 LO3 | 23.62 |
| PMA-Test article 7 LO13 | 21.11 |
| PMA-Test article 8 SPC19 | 22.11 |
| PMA-Test article 9 Zileuton 1.0% cream | 15.08 |

The invention claimed is:

1. A topical anti-inflammatory pharmaceutical composition, comprising Zileuton at a concentration of >2% (w/w), wherein the pharmaceutical composition is formulated as a lotion and further comprises an organic solvent.

2. The composition according to claim 1, wherein Zileuton is present at a concentration in the range of from 4.5% (w/w) to 5.5% (w/w).

3. The composition according to claim 1, wherein Zileuton is racemic Zileuton.

4. A method of treatment of a skin disease, wherein said method comprises administering, to a subject in need of such treatment, a composition of claim 1.

5. The method according to claim 4, wherein said skin disease is selected from atopic dermatitis, acne, urticaria, psoriasis, eczema, a bullous skin disease, collagenoses, Sjogren-Larsson syndrome, and acne in skin lesions of mastocytosis.

6. The method according to 4, wherein the composition is applied topically to human skin.

7. A method of preparing a topical anti-inflammatory pharmaceutical composition according to claim 1, said method comprising the following steps: heating ingredients and solvents, mixing Zileuton and dissolved ingredients as well as cooling mixed Zileuton and ingredients, wherein the ingredients comprise one or more of an emulsifier and an oil, and wherein the solvents are selected from organic solvents and aqueous solvents.

8. The method according to claim 7, said method comprising the following steps: heating ingredients and solvents under heating condition of temperature of 50° C. to 70° C., mixing Zileuton and dissolved ingredients under mixing condition of temperature of 50° C. to 70° C. with 1000 rpm to 1500 rpm of mixing speed as well as cooling mixed Zileuton and ingredients to 20° C. to 30° C.

9. The composition according to claim 1, wherein the composition further comprises at least one of an aqueous solvent, an emulsifier and an oil.

10. The composition according to claim 1, wherein the organic solvent is present in said composition in a range of from 10% (w/w) to 80% (w/w).

11. The composition according to claim 9, wherein the organic solvent is present in said composition in a range of from 45% (w/w) to 55% (w/w), the aqueous solvent is present in said composition in a range of from 18% (w/w) to 22% (w/w) and/or the emulsifier is present in said composition in a range of from 23% (w/w) to 27% (w/w).

12. The composition according to claim 1, wherein the organic solvent is selected from ethanol, diethylene glycol monoethyl ether, propylene glycol, hexylene glycol, polyethylene glycol 200, polyethylene glycol 300, polyethylene glycol 400, polyethylene glycol 1500, polyethylene glycol 3350, N-methyl-2-pyrrolidone, dimethyl formamide, dimethyl acetamide, and mixtures of any of the foregoing.

13. The composition according to claim 9, wherein the aqueous solvent is water or a pH buffered solution in a range from pH 2.0 to 8.0.

14. The composition according to claim 9, wherein the emulsifier is selected from sorbitan monolaurate, caprylo-caproyl polyoxylglycerides, sodium lauryl sulfate, polyethylene glycol octadecyl ether, lecithin from soybean, poly-oxyl 35 hydrogenated castor oil, polyethylene glycol-40 hydrogenated castor oil, polyoxyethylenesorbitan monoste-arate, poly-oxyethylene esters of 12-hydroxystearic acid, polyoxyethylenesorbitan monooleate, d-a-tocopheryl poly-ethylene glycol 1000 succinate, triethanolamine, propylene glycol monolaurate, and mixtures of any of the foregoing.

15. The composition according to claim 9, wherein the oil is selected from glyceryl monocaprate type I, propylene glycol monocaprylate type II, caprylocaproyl polyoxyl glyc-erides, and mixtures of any of the foregoing.

16. The composition according to claim 9, wherein the composition comprises an organic solvent, an aqueous solvent and an emulsifier.

17. The composition according to claim 1, wherein the organic solvent is present in said composition in a range of from 13% (w/w) to 77% (w/w).

18. The composition according to claim 13, wherein the pH buffered solution is selected from acid phthalate buffer (pH 4.0), acetate buffer (pH 4.1), citrate buffer (pH 4.0), phosphate buffer (pH 6.0) and merck buffer pH (4.0).

\*   \*   \*   \*   \*